US008846595B2

(12) United States Patent
Ylitalo et al.

(10) Patent No.: US 8,846,595 B2
(45) Date of Patent: Sep. 30, 2014

(54) METHOD OF MAKING A CLEANING SOLUTION FROM HYDROGEL CLEANING CONCENTRATE AND PACKAGED CLEANING CONCENTRATE

(75) Inventors: Caroline M. Ylitalo, Stillwater, MN (US); Robin E. Wright, Inver Grove Heights, MN (US); Sonja K. Belgrade, Stillwater, MN (US); Mitchell T. Johnson, Gig Harbor, WA (US); Richard L. Walter, St. Paul, MN (US); John M. Brandner, St. Paul, MN (US); Narina Y. Stepanova, Inver Grove Heights, MN (US); James W. Zurawski, St. Anthony, MN (US)

(73) Assignee: 3M Innovative Properties Company, St. Paul, MN (US)

(*) Notice: Subject to any disclaimer, the term of this patent is extended or adjusted under 35 U.S.C. 154(b) by 252 days.

(21) Appl. No.: 12/992,139

(22) PCT Filed: Jun. 12, 2009

(86) PCT No.: PCT/US2009/047145

§ 371 (c)(1),
(2), (4) Date: Nov. 11, 2010

(87) PCT Pub. No.: WO2010/008712

PCT Pub. Date: Jan. 21, 2010

(65) Prior Publication Data

US 2011/0082068 A1 Apr. 7, 2011

Related U.S. Application Data

(60) Provisional application No. 61/080,506, filed on Jul. 14, 2008.

(51) Int. Cl.

| | |
|---|---|
| ***C11D 17/00*** | (2006.01) |
| ***C11D 3/00*** | (2006.01) |
| ***A61K 8/04*** | (2006.01) |
| ***C11D 3/37*** | (2006.01) |
| ***C11D 17/04*** | (2006.01) |

(52) U.S. Cl.

CPC ............ *C11D 3/3707* (2013.01); *C11D 17/041* (2013.01); *C11D 17/0034* (2013.01)

USPC ........... 510/294; 510/113; 510/120; 510/224; 510/396; 510/439

(58) Field of Classification Search

USPC .................. 510/113, 120, 224, 294, 396, 439

See application file for complete search history.

(56) References Cited

U.S. PATENT DOCUMENTS

| | | | |
|---|---|---|---|
| 4,203,851 | A | 5/1980 | Ramachandran |
| 4,659,496 | A | 4/1987 | Klemm et al. |

(Continued)

FOREIGN PATENT DOCUMENTS

| | | |
|---|---|---|
| EP | 0257966 | 3/1988 |
| EP | 385 529 | 9/1990 |

(Continued)

OTHER PUBLICATIONS

International Search Report PCT/US2009/047145; Aug. 18, 2009, 4 pgs.

(Continued)

*Primary Examiner* — Ling Choi
*Assistant Examiner* — Thuy-Ai Nguyen
(74) *Attorney, Agent, or Firm* — Carolyn A. Fischer

(57) ABSTRACT

Methods of making a (e.g. dilute) cleaning solution from a hydrogel cleaning concentrate, packages of hydrogel cleaning concentrate, and methods of making a hydrogel cleaning concentrate are described.

23 Claims, 5 Drawing Sheets

(56) References Cited

U.S. PATENT DOCUMENTS

| | | | |
|---|---|---|---|
| 4,929,400 | A | 5/1990 | Rembaum et al. |
| 4,946,617 | A | 8/1990 | Sheridan et al. |
| 4,973,416 | A | 11/1990 | Kennedy |
| 5,126,381 | A | 6/1992 | Liscomb |
| 5,294,361 | A | 3/1994 | Van den Brom |
| 5,506,279 | A | 4/1996 | Babu et al. |
| 5,514,379 | A | 5/1996 | Weissleder et al. |
| 5,674,521 | A | 10/1997 | Gehrke et al. |
| 6,040,286 | A | 3/2000 | Huff |
| 6,090,763 | A | 7/2000 | Stewart et al. |
| 6,133,214 | A | 10/2000 | Jung et al. |
| 6,250,511 | B1 | 6/2001 | Kelly |
| 6,399,555 | B2 | 6/2002 | Robbins et al. |
| 6,451,750 | B2 | 9/2002 | Hewitt et al. |
| 6,729,786 | B1 | 5/2004 | Tufts et al. |
| 6,787,512 | B1 | 9/2004 | Verrall et al. |
| 6,800,278 | B1 * | 10/2004 | Perrault et al. ............. 424/78.06 |
| 6,808,738 | B2 | 10/2004 | DiTizio et al. |
| 6,861,067 | B2 | 3/2005 | McGhee et al. |
| 6,939,836 | B2 | 9/2005 | Kritzler et al. |
| 6,946,501 | B2 | 9/2005 | Kochvar et al. |
| 6,995,128 | B2 | 2/2006 | Mitra et al. |
| 7,005,143 | B2 | 2/2006 | Abuelyaman et al. |
| 7,074,750 | B2 * | 7/2006 | Hamers et al. ................ 510/400 |
| 7,115,173 | B2 | 10/2006 | Caswell et al. |
| 7,169,740 | B2 | 1/2007 | Sommerville-Roberts et al. |
| 7,259,134 | B2 | 8/2007 | Deckholt et al. |
| 7,318,871 | B2 | 1/2008 | Egan et al. |
| 7,325,688 | B1 | 2/2008 | Tessmer et al. |
| 2005/0215752 | A1 | 9/2005 | Popp et al. |
| 2005/0287191 | A1 * | 12/2005 | Munro et al. ................. 424/443 |
| 2006/0051384 | A1 | 3/2006 | Scholz et al. |
| 2006/0051385 | A1 | 3/2006 | Scholz |
| 2006/0052452 | A1 | 3/2006 | Scholz |
| 2006/0212011 | A1 | 9/2006 | Popp et al. |
| 2006/0235141 | A1 | 10/2006 | Riegel et al. |
| 2006/0242754 | A1 * | 11/2006 | Coppock ........................... 4/224 |
| 2006/0280546 | A1 | 12/2006 | Dyer |
| 2007/0238634 | A1 | 10/2007 | Foland et al. |
| 2008/0207794 | A1 | 8/2008 | Wright et al. |

FOREIGN PATENT DOCUMENTS

| | | |
|---|---|---|
| EP | 518 689 | 3/1999 |
| EP | 1714605 | 10/2006 |
| GB | 1501324 | 2/1978 |
| JP | S63-317597 | 12/1988 |
| JP | 2001-515955 | 9/2001 |
| WO | 89/04284 | 5/1989 |
| WO | 96/29979 | 10/1996 |
| WO | 02/102951 | 12/2002 |
| WO | 2005/041659 | 5/2005 |
| WO | 2006/028582 | 3/2006 |
| WO | 2007/143344 | 12/2007 |
| WO | 2007/146635 | 12/2007 |
| WO | 2007/146722 | 12/2007 |
| WO | 2009/076267 | 6/2009 |

OTHER PUBLICATIONS

3M™ Material Safety Data Sheet Exp Liquid Cleaning Solution; Feb. 7, 2008, 8 pgs.

Material Safety Data Sheet 3M™ Neutral Quat Disinfectant Cleaner Concentrate (Product No. 23, Twist 'n Fill™ System; Jun. 10, 2008.

Material Safety Data Sheet 3M™ Bathroom Disinfectant Cleaner (Concentrate) (Product No. 4, Twist 'n Fill™ System) Jun. 9, 2008.

Material Safety Data Sheet 3M™ Neutral Cleaner Lo Concentrate (Product No. 33, Twist 'n Fill™ System) Jul. 11, 2007.

Washington State Department of Agriculture, Assigned Active Ingredients in Bardac 208M (Jun. 19, 2008).

Washington State Department of Agriculture, Assigned Active Ingredients in Bardac 205M (Jun. 19, 2008).

3M™ Twist 'n Fill™ Cleaning Chemical Management System; undated, 8 pgs.

* cited by examiner

METHOD OF MAKING A CLEANING SOLUTION FROM HYDROGEL CLEANING CONCENTRATE AND PACKAGED CLEANING CONCENTRATE

CROSS REFERENCE TO RELATED APPLICATIONS

This application is a national stage filing under 35 U.S.C. 371 of PCT/US2009/047145, filed Jun. 12, 2009, which claims priority to U.S. Provisional Application No. 61/080,506, filed Jul. 14, 2008, the disclosure of which is incorporated by reference in its entirety herein.

SUMMARY

In one embodiment, a method of making a cleaning solution is described. The method comprises providing a mass of a hydrogel cleaning concentrate, the hydrogel comprising an active cleaning component and a homogeneous mixture of a water insoluble polymer and polar solvent; combining the hydrogel cleaning concentrate with water in an amount of at least 10 times the mass of hydrogel cleaning concentrate to form a cleaning solution.

The method typically further comprises separating the insoluble polymer of the hydrogel from the cleaning solution. In some embodiments, the hydrogel cleaning concentrate and water are combined in a receptacle and the receptacle comprises a means for separating the insoluble polymer from the cleaning solution. Alternatively or in addition thereto, the hydrogel cleaning concentrate can be contained within a water permeable and water insoluble enclosure (such as a disposable pouch or refillable cartridge) wherein the enclosure is combined with the water. In such exemplary embodiments, the enclosure may thereby provide a means for separating the insoluble polymer of the hydrogel from the cleaning solution.

The cleaning solution typically reaches a target concentration (e.g. ready to use) in less than 15 minutes and preferably in less than 1 minute. The water can be statically or dynamically combined with the hydrogel cleaning concentrate. In some embodiments, the hydrogel cleaning concentrate is separated from the cleaning solution and recombined with additional water to form at least one second cleaning solution.

In another embodiment, a package of hydrogel cleaning concentrate is described. The package comprises a mass of hydrogel cleaning concentrate contained by a water permeable (and preferably water insoluble) enclosure wherein the hydrogel cleaning concentrate comprises an active cleaning component and a homogeneous mixture of a water insoluble polymer and polar solvent.

The active cleaning component of the hydrogel cleaning concentrate comprises a surfactant, an enzyme, an acid, a base, or mixtures thereof. The hydrogel cleaning concentrate may further comprise various adjuncts such as an antimicrobial agent or fragrance. The hydrogel cleaning concentrate of the method or package may be provided as a unitary shaped mass, but typically as a plurality of discrete free-flowing pieces such as beads, fibers, or (e.g. crushed) particles. In some embodiments, the hydrogel cleaning concentrate of the method or package comprises a first mass of hydrogel cleaning concentrate comprising a first active cleaning component and a second mass of hydrogel cleaning concentrate comprising a different active cleaning component than the first mass. The mass of hydrogel cleaning concentrate may be premeasured to a proper amount for a specified amount of water (e.g. such as the capacity of a receptacle in which the hydrogel cleaning concentrate and water are combined). In some embodiments, the hydrogel cleaning concentrate is combined with an effervescent agent.

In another embodiment, a method of making a hydrogel bead is described. The method comprises providing a precursor composition comprising: a) greater than 10 weight percent polar solvent based on a total weight of the precursor composition, b) a polymerizable material capable of free-radical polymerization and having an average number of ethylenically unsaturated groups per monomer molecule equal to at least 1.2, wherein the polymerizable material is miscible with the polar solvent, and c) an active cleaning component, wherein a) in combination with c) has a surface energy of no greater than 30 mN/m; forming a droplet of the precursor composition, wherein the droplet is totally surrounded by a gas phase; and exposing the droplet to radiation for a time sufficient to at least partially polymerize the polymerizable material and to form a first hydrogel cleaning concentrate bead. The method optionally further comprises drying the first hydrogel cleaning concentrate bead and combining the dried bead with (the same or a different) active cleaning component to form a second swollen hydrogel cleaning concentrate bead (e.g. having a higher concentration of active cleaning component than the first). In some embodiments, the polymerizable material comprises poly(alkylene oxide) units. The poly(alkylene oxide) units of the polymerizable material preferably have at least 5 alkylene oxide subunits and/or have a weight average molecular weight no greater than 2000 g/mole.

In each of these embodiments, the water insoluble polymer of the hydrogel is preferably a free radically polymerized polymer. The hydrogel precursor composition preferably further comprises a photoinitiator and the water insoluble polymer is preferably a radiation cured polymer. The water insoluble polymer preferably comprises poly(alkylene oxide) units. The hydrogel cleaning concentrate may comprise about 25 wt-% to 70 wt-% of the water insoluble polymer and 30 wt-% to 75 wt-% of the polar solvent.

DETAILED DESCRIPTION

Figure 1:
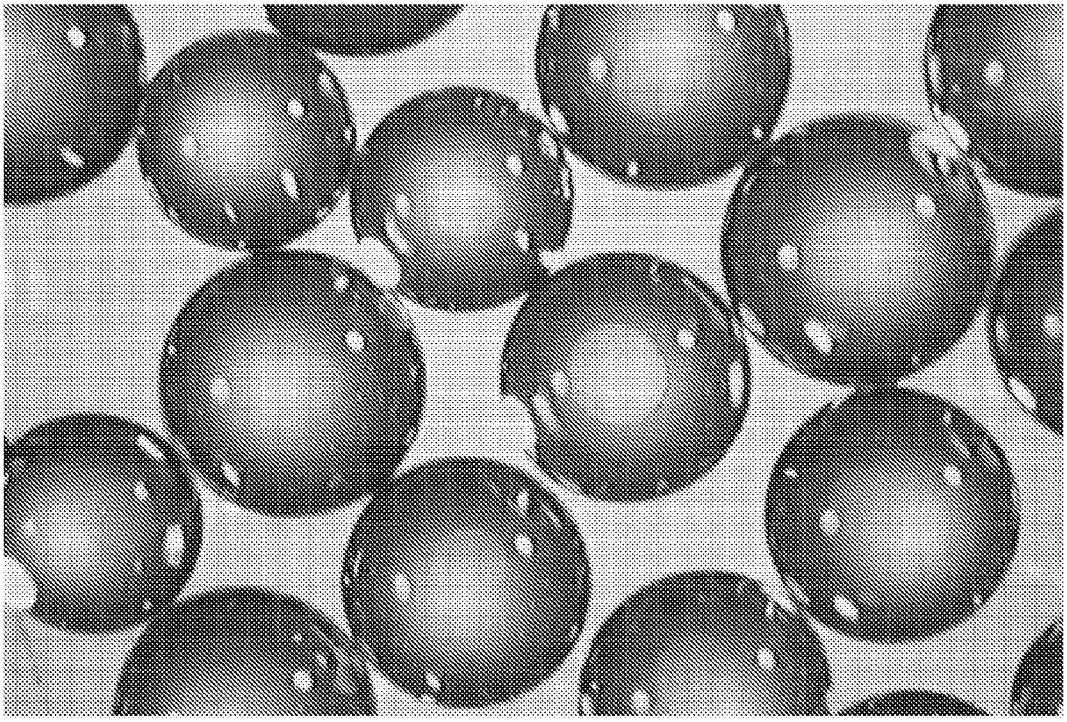
FIG. 1 is an optical micrograph at a magnification of 200 times of an embodiment of a hydrogel cleaning concentrate in the form of polymeric beads.

Presently described are methods of making a (e.g. dilute) cleaning solution from a hydrogel cleaning concentrate, packages of hydrogel cleaning concentrate, and methods of making a hydrogel cleaning concentrate.

The method of making a cleaning solution generally comprises providing a hydrogel cleaning concentrate and combining the hydrogel cleaning concentrate with water. The hydrogel cleaning concentrate comprises an active cleaning component and a homogeneous mixture of a water insoluble polymer and a polar solvent. Once the hydrogel cleaning concentrate is combined with water, the active cleaning component diffuses from the hydrogel into the water to form a cleaning solution. The cleaning solution thus formed comprises a diluted concentration of active cleaning component relative to the concentration of active cleaning component in the hydrogel cleaning concentrate.

Various active cleaning components can be employed in the hydrogel cleaning concentrate. Active cleaning component refers to at least one component that aids in the dissolution of organic or inorganic contaminants into a polar solvent, preferably water. The most common active cleaning components include surfactants, acids, bases, and enzymes.

Typically the cleaning concentrate of the hydrogel is sufficiently concentrated such that the hydrogel cleaning concentrate is combined with water in an amount of at least 10, 20, 30, 40, or 50 times the mass of the hydrogel. For hydrogels comprising a high concentration of active cleaning component(s) or those comprising an active cleaning component(s) that is effective at very dilute concentrations, the amount of water may be 100, 200, 300, 400 or even 500 times the mass of the hydrogel cleaning concentrate.

The cleaning solution can be a "ready to use" ("RTU") solution, i.e. the concentration at which the cleaning solution is used to clean a surface. Alternatively, the cleaning solution can be an intermediate concentrate from which an even more dilute or RTU cleaning solution is formed.

The RTU cleaning solution can be applied to any suitable inorganic, polymeric, metal or composite surface including but not limited to countertops, cabinets, (e.g. enamel or stainless steel) appliance surfaces, (e.g. wood, vinyl, laminate) flooring, driveways and sidewalks, siding or other exterior construction surfaces, glass and mirrors, ceramic, tile and the like.

As used herein, the term "hydrogel" refers to a polymeric material that is hydrophilic and that is either swollen or capable of being swollen with a polar solvent. The polymeric material typically swells but does not dissolve when contacted with the polar solvent. That is, the hydrogel is insoluble in the polar solvent.

The hydrogel cleaning concentrate can be provided in any physical form. In some embodiments, the hydrogel cleaning concentrate is provided as a (e.g. unitary) shaped mass such as described in U.S. Patent Application 61/013,085 filed Dec. 12, 2007. In other embodiments, the hydrogel cleaning concentrate is provided as a plurality of discrete (e.g. free-flowing) pieces such as hydrogel beads or fibers. (See for example Published U.S. Patent Application US2008/0207794 and WO 2007/146722; each incorporated herein by reference). Discrete free-flowing pieces of hydrogel cleaning concentrate can also be formed by crushing a larger mass of hydrogel cleaning concentrate. When hydrogel particles are prepared by processes such as milling or grinding the particles typically have irregular surfaces. The pieces typically range in size from about 0.5 mm to about 5 mm and more typically from about 1 mm to about 3 mm. When crushed, the particle size can be 50 micrometers or less. When provided as a unitary shaped mass, the hydrogel mass can have considerably larger dimensions. For example shaped hydrogel cylindrical sticks (e.g. for use in a 22 oz spray bottle) may have a diameter from about 1.5 mm to 5 mm and a height up to about 10 mm or greater. Alternatively, the hydrogel cleaning concentrate can be provided in the form of substantially continuous fiber such as described in U.S. patent application Ser. No. 11/847,397 filed Aug. 30, 2007.

When the hydrogel cleaning concentrate is provided as a plurality of free-flowing pieces, the same hydrogel cleaning concentrate can conveniently be used to produce any volume of RTU cleaning solution by simply measuring the correct amount for the intended amount of water that will be added. In the same fashion, various premeasured packages of hydrogel cleaning concentrate can be made. Thus, packages with relatively large amounts of hydrogel cleaning concentrate can be made for industrial uses in which an intermediate concentrate is formed. Likewise, packages with small amounts can be made for residential consumer uses.

The insoluble polymer of the hydrogel provides diffusion-controlled transport both into and from the bulk. The rate of diffusion can be controllable by, for example, varying the polymeric material and the crosslink density, by varying the polar solvent, by varying the solubility of the active cleaning component in the polar solvent, and by varying the molecular weight of the active cleaning component. Increasing or decreasing the surface area of the hydrogel as well as increasing the temperature of the water the hydrogel cleaning concentrate is combined with also affects the rate of diffusion. When a mass of hydrogel is provided as a plurality of discrete pieces the hydrogel has a higher surface area relative to being provided as a single piece having the same mass.

It is preferred that once the hydrogel cleaning concentrate has been combined with an appropriate amount of water, the cleaning solution reaches a (e.g. RTU) target concentration in a relatively short duration of time. Typically, the target concentration is obtained in less than 1 hour. Preferably, the active cleaning component diffuses at a sufficient rate such that the target concentration is obtained in no greater than 30 minutes, 15 minutes, 10 minutes, 5 minutes, or no greater than 1 or 2 minutes.

The hydrogels can be prepared as described in WO 2007/146722; incorporated herein by reference. The hydrogel is formed from a precursor composition, i.e. a reaction mixture prior to polymerization. In some embodiments, the precursor composition comprises a cleaning concentrate, wherein the cleaning concentrate comprises a polar solvent and at least one active cleaning component, and a polymerizable material that is miscible with the polar solvent. Although the polar solvent is not reactive in the precursor composition (i.e., the polar solvent is not a monomer), the hydrogel is swollen with the polar solvent.

Alternatively, the hydrogel may be formed from a precursor composition that contains a polar solvent, but lacks an active cleaning component or lacks a sufficient concentration of active cleaning component(s). The hydrogel can be dried to evaporate at least a portion of the polar solvent. The dried hydrogel can then be contacted with a liquid cleaning concentrate for a time sufficient to sorb at least a portion of the cleaning concentrate. The cleaning concentrate sorbate comprises at least a polar solvent and at least one active cleaning component. As used herein, the term "sorb" refers to adsorb, absorb, or a combination thereof. Likewise, the term "sorption" refers to adsorption, absorption, or a combination thereof. The sorption can be a chemical process (i.e., a chemical reaction occurs), a physical process (i.e., no chemical reaction occurs), or both.

To increase the concentration of active cleaning component in the hydrogel, in some embodiments it is preferred to prepare the hydrogel from a precursor comprising active cleaning component, dry the hydrogel cleaning concentrate and then contact the dried hydrogel with additional or a different cleaning concentrate to sorb additional active cleaning component into the hydrogel. The hydrogel may repeatedly be dried and swelled with cleaning concentrate solution. For example, this cycle can be repeated 2, 3, 4, or 5 times or until the hydrogel is substantially saturated with active cleaning component. The increase in active cleaning component in the dried hydrogel is equal to the amount of liquid cleaning concentrate absorbed multiplied by the concentration of active cleaning component in the liquid cleaning concentrate sorbate.

The dried hydrogel can often sorb an amount of liquid cleaning concentrate sorbate that is equal to at least 10 weight percent, at least 20 weight percent, at least 40 weight percent, at least 50 weight percent, at least 60 weight percent, at least 80 weight percent, at least 100 weight percent, at least 120 weight percent, at least 140 weight percent, at least 160 weight percent, at least 180 weight percent, or at least 200 weight percent based on the weight of the dried hydrogel. The weight increase is typically less than 300 weight percent, less than 275 weight percent, or less than 250 weight percent.

When the active cleaning component is present in the hydrogel precursor composition, the active cleaning component is typically also distributed homogeneously. However, when hydrogel cleaning concentrate is prepared by sorption of an active cleaning component into a dried hydrogel, the active cleaning component may not be distributed homogeneously throughout the polymeric bead. Further, the active cleaning component may be present in a separate phase from the polymeric matrix.

In many embodiments, the hydrogel cleaning concentrate will be described herein with reference to one illustrative physical form, i.e. hydrogel beads. It is appreciated however, that other physical forms can be used in lieu of hydrogel cleaning concentrate beads.

As used herein, the terms "bead" and "polymeric bead" are used interchangeably and refer to a particle that contains polymeric material, that preferably has a smooth surface, and that in some embodiments has an aspect ratio no greater than 3:1, no greater than 2.5:1, no greater than 2:1, no greater than 1.5:1, or 1:1. That is, the aspect ratio is preferably in the range of 3:1 to 1:1. The aspect ratio refers to the ratio of the longest dimension of the polymeric bead to the dimension orthogonal to the longest dimension. The shape of the polymeric bead is often spherical or elliptical; however, the spherical or elliptical shape can be collapsed when the polymeric bead is dried. As used herein, the term "smooth" refers to a surface that is free of discontinuities and sharp edges when viewed under a microscope such as an optical microscope (50 times magnification).

With reference to FIG. 1, by homogeneous it is meant that there is no discernible interface between the outer surface and the inner composition when viewed under a microscope such as an optical microscope (50 times magnification). In some embodiments, no discernible interface is evident when viewed by a scanning electron microscope (50,000 times magnification). The dried polymeric beads often remain homogeneous and do not contain internal pores or channels such as macroscopic (i.e., greater than 100 nm) pores or channels.

The water insoluble polymer is relatively insensitive to humidity. When provided as a plurality of discreet pieces such as beads, the beads do not block together forming a single mass during storage. The hydrogel cleaning concentrate typically feels dry to the touch. Accordingly, the hydrogel cleaning concentrate advantageously provides a means for dry delivery of liquid cleaning concentrates.

The water insoluble polymer of the hydrogel is not solvated by the water employed to form the cleaning solution or by the cleaning solution formed and thus does not become a component of the cleaning solution. This can be advantageous since a water soluble polymeric binder typically leaves a residue after evaporation of the water from the cleaning solution. However, since the hydrogel comprises a water insoluble polymer (e.g. binder) component, the method of making a cleaning solution preferably comprises separating the insoluble polymer of the hydrogel from the cleaning solution in order that the water insoluble polymer does not clog the dispenser for the cleaning solution.

The hydrogel cleaning concentrate or cleaning solution thus formed can be used with any (e.g. mop, spray bottle, industrial etc.) applicator system.

In some embodiments, the hydrogel cleaning concentrate and water are combined in a (e.g. reuseable) receptacle. The receptacle may be designed to be coupled to a dispensing system for the cleaning solution. The receptacle or dispensing system may comprise a means for separating the insoluble polymer of the hydrogel from the cleaning solution.

Figure 2:
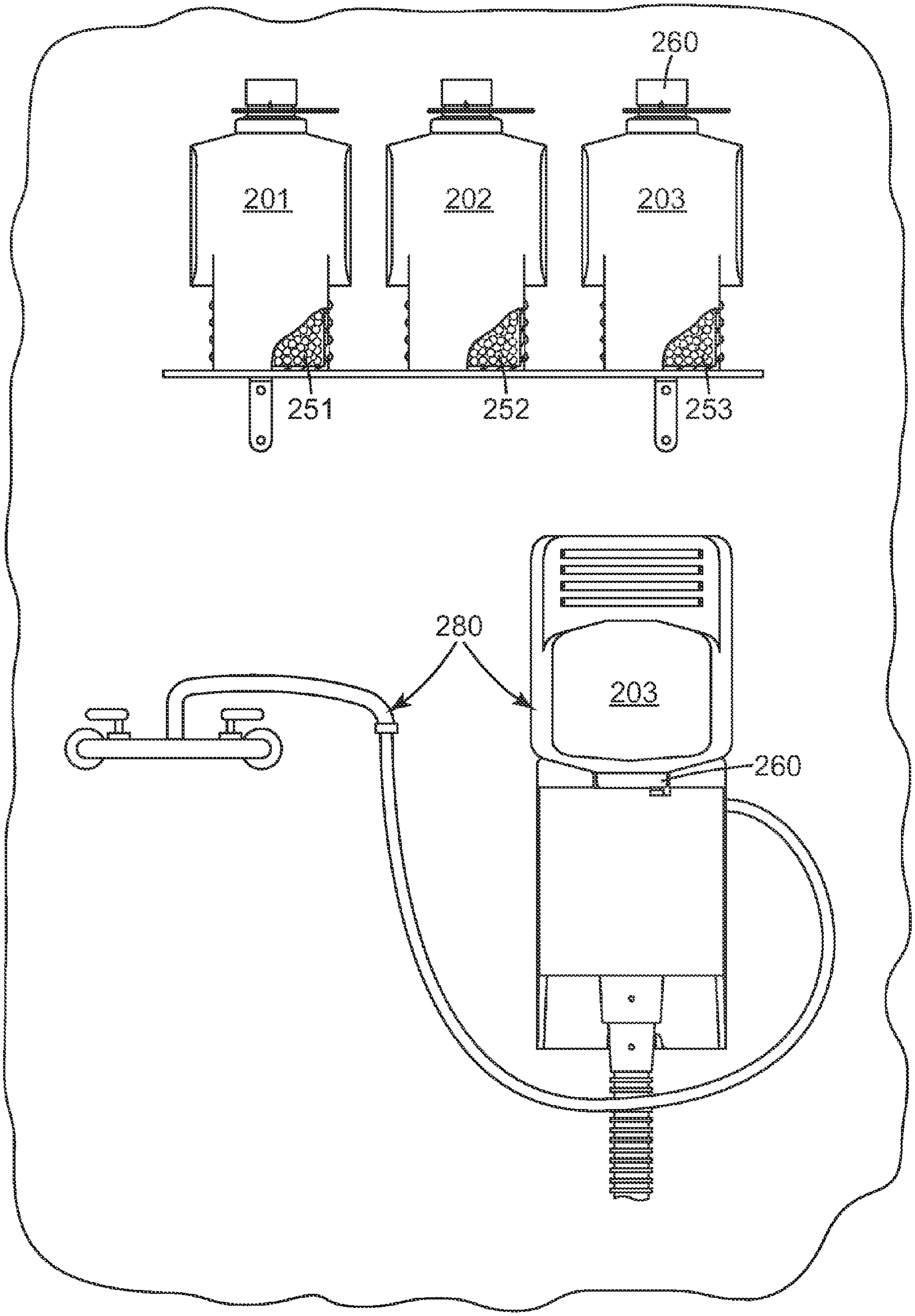
FIG. 2 depicts a cleaning system including receptacles comprising a hydrogel cleaning concentrate and a water dispensing system.

For example, FIG. 2 illustrates one approach of utilizing the hydrogel cleaning concentrates described herein in a conventional gravity fed system designed for dilution of liquid concentrated cleaners. FIG. 2 depicts 3M™ Twist n' Fill™ Cleaning Chemical Management System comprising several bottles 201, 202, 203, each comprising different hydrogel cleaning concentrate beads 251, 252, and 253 respectively. The hydrogel cleaning concentrate is first combined with water in the bottles to form an intermediate cleaning concentrate solution. By intermediate, it is meant that the cleaning concentrate is further diluted to form the RTU cleaning solution. After the intermediate cleaning concentrate is formed, a bottle (e.g. 203) is inverted and coupled with a water dispensing system 280 for dilution to the RTU cleaning solution concentration. In one embodied means of separating the insoluble polymer of the hydrogel from the intermediate cleaning concentrate solution, the cap 260 of the bottle includes a screen (not shown) for filtering the water insoluble polymer of the hydrogel from the cleaning solution.

The receptacle for the (e.g. intermediate or RTU) cleaning solution is not limited to a bottle. Any non-deformable or (e.g. squeezable) deformable container that can hold fluid can be used. For example, the receptacle may comprise a bag, pouch, or bag-in-a-box container. Further, the receptacle may comprise a single chamber or more than one chamber, thereby permitting the contents of multiple chambers to react, combine or mix prior to or concurrent with being dispensed.

As an alternative to directly combining the mass of hydrogel cleaning concentrate with water, a mass of hydrogel cleaning concentrate can be contained within a water permeable enclosure such as a (e.g. refillable) cartridge or (e.g. premeasured) package of hydrogel cleaning concentrate. The enclosure (e.g. cartridge or package) is combined with water. Any structure can be used as an enclosure according to the present disclosure, provided the structure is capable of containing the mass of hydrogel therein. The enclosure may be disposable, containing a (e.g. free-flowing) premeasured mass of hydrogel cleaning concentrate disposed within its interior. Alternatively the enclosure may be reusable (i.e. refillable), having an opening capable of repeatedly being opened and then maintained in a closed state to retain the contents of the insoluble polymer of the hydrogel.

Although the water permeable enclosure could be prepared from a water soluble polymer such as polyvinyl alcohol, the enclosure is preferably configured to retain the insoluble polymer of the hydrogel cleaning concentrate. In preferred embodiments, the enclosure is water insoluble as well as insoluble in the cleaning solution. The enclosure can then be removed together with the insoluble polymer from the cleaning solution before or after the cleaning solution has been dispensed.

Various water insoluble plastic, ceramic, metal, and composite materials can be used to make the enclosure. In order to retain the insoluble polymer of the hydrogel, the openings or pore size of the enclosure are sufficiently smaller than the physical form of the hydrogel (e.g. unitary mass or beads).

In some embodiments, the enclosure comprises a premeasured mass of hydrogel cleaning concentrate. In this embodiment, the enclosure is typically configured to be disposable. For example, various commercially available nonwoven materials can be heat sealed into pouches containing the hydrogel cleaning concentrate therein. Suitable nonwoven materials include for example spunbond polypropylene (20 grams/$m^2$), spunbond polyester (15 grams/$m^2$) commercially available from BBA Fiberweb (Old Hickory, Tenn.), and spunbond nylon (17 grams/$m^2$) nonwoven commercially available from Cerex Advanced Fabrics, Inc (Pensacola, Fla.).

Figure 3:
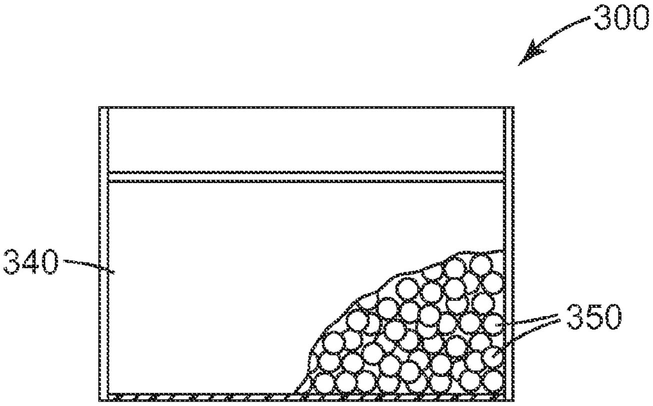
FIG. 3 is an embodiment of a package of hydrogel cleaning concentrate beads contained in an enclosure.

FIG. 3 illustrates one embodiment of a package 300 comprising a premeasured mass of hydrogel cleaning concentrate beads 350 contained within a water permeable (e.g. nonwoven) enclosure 340.

Figure 4:
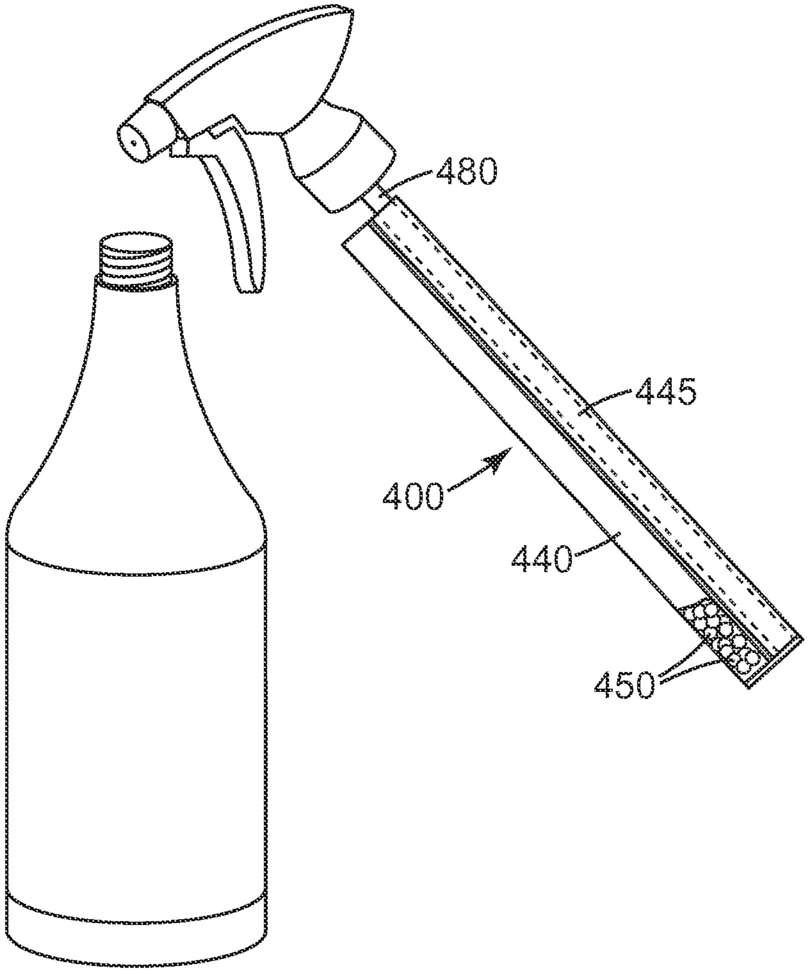
FIG. 4 is another embodiment of a package of hydrogel cleaning concentrate beads contained in an elongated enclosure including a sleeve for attachment to the shaft of a spray bottle.

FIG. 4 illustrates another embodiment of a package 400 of hydrogel cleaning concentrate comprising a premeasured mass of hydrogel cleaning concentrate beads 450 contained within a rectangular shaped water permeable (e.g. nonwoven) enclosure 440. The package further comprises a sleeve 445 for attachment to the shaft 480 of a spray bottle.

Figure 5:
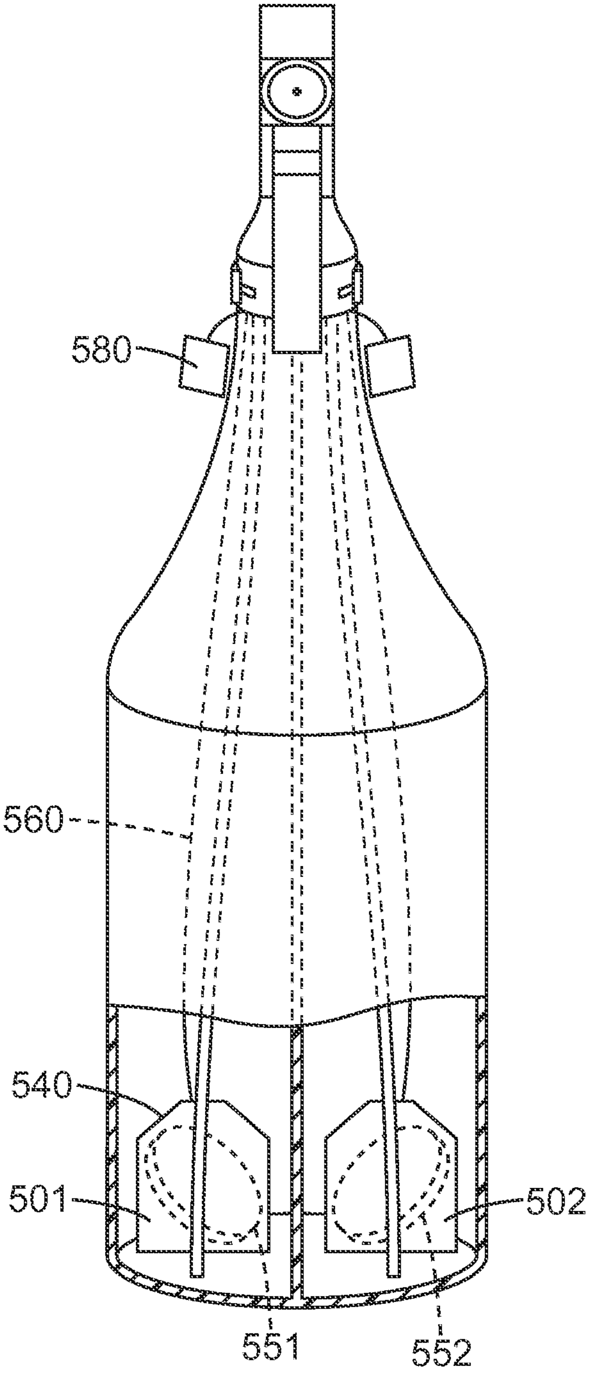
FIG. 5 depicts a dual chamber spray bottle, each chamber comprising a different hydrogel cleaning concentrate unitary mass in the shape of a disk, the disk contained within a package—here, a "tea bag" type enclosure.

FIG. 5 illustrates another embodiment of packages 501 and 502, each package containing a unitary shaped mass of hydrogel cleaning concentrate, 551 and 552, in the form of a disk, wherein each disk is enclosed in a "tea bag" type nonwoven enclosure 440. In this embodiment, each package further comprises a string 560 and tab 580 for removing the packages from the cleaning solution. WO 2007/146635 describes another suitable (e.g. mop) application system suitable for concurrently applying two different cleaning solutions.

In some embodiments, the enclosure is reusable (e.g. refillable). Refillable pouches may also be fabricated from various durable screen or mesh materials comprised of for example aluminum, stainless steel or durable plastic materials such as nylon. The edges of the pouch can be fastened with any suitable means such as for example stitching or adhesive bonding. Further, thermoplastic materials can be bonded by ultrasonic welding and heat sealing. Along one peripheral edge of the pouch, an interlocking closure system (e.g. zipper, hook and loop) can be provided in order that the pouch can be repeatedly opened and closed. Various molded (e.g. plastic) cartridges that are suitable enclosures for this purpose are known in the art.

Figure 6A:
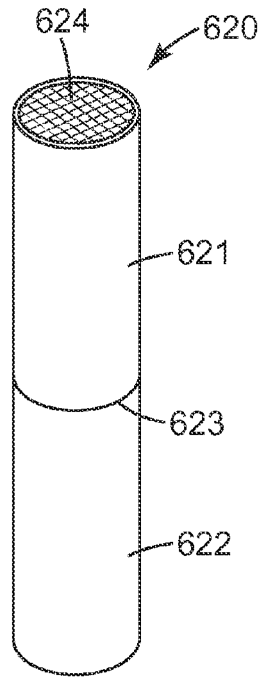
FIG. 6*a* depicts a refillable cartridge package for containing hydrogel cleaning concentrate, the cartridge suitable for insertion into a mop handle.
Figure 6B:
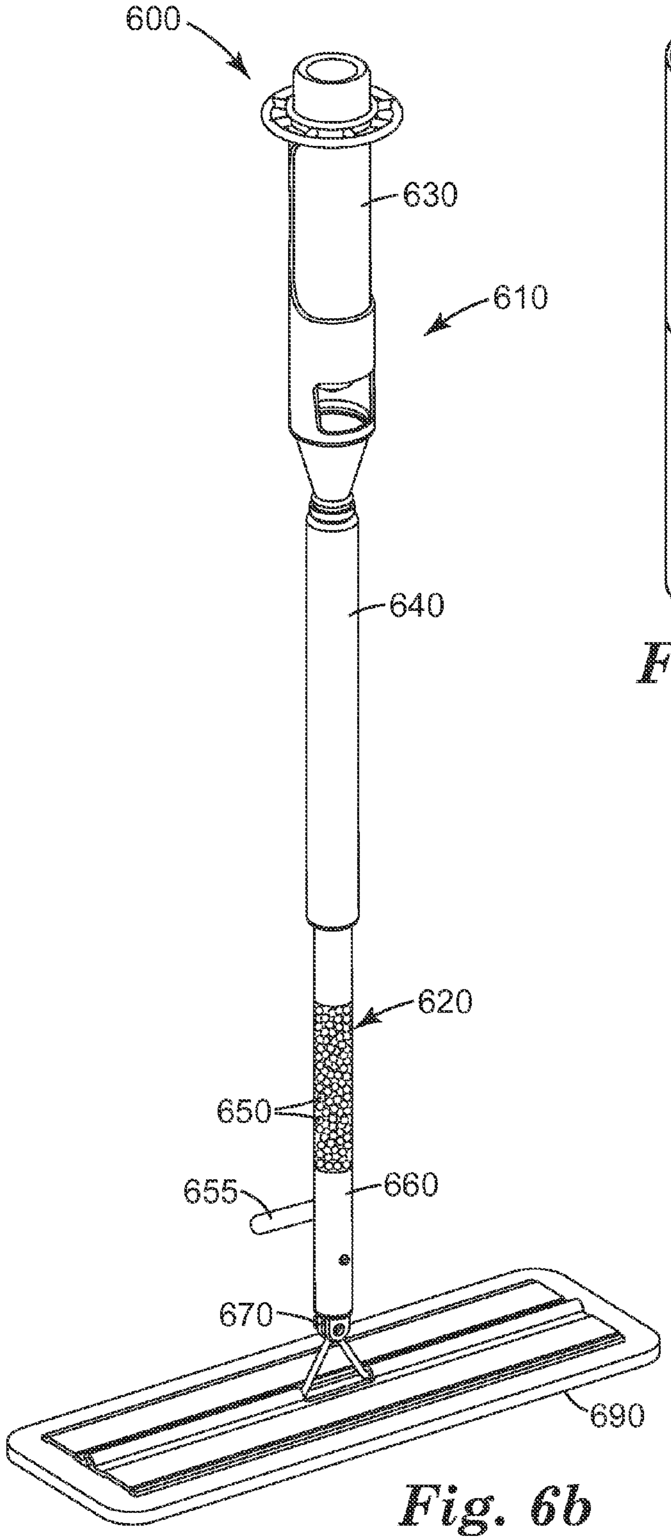
FIG. 6*b* depicts an embodied mop.

FIG. 6*a* illustrates a perspective view of an embodiment of a refillable plastic cartridge enclosure 620 suitable for containing an amount of hydrogel cleaning concentrate. The cartridge has two parts 621 and 622, the parts being connected at joint 623. The cartridge parts may be threaded or one part may have a smaller diameter relative to the other part in order that the parts can be joined securely. The top of the refillable molded plastic cartridge can be turned to open the cartridge in order to place a unitary shaped mass or a plurality of discrete pieces (e.g. beads) 650 of hydrogel cleaning concentrate within the cartridge. The top and bottom (not shown) of the cartridge comprises a (e.g. plastic) mesh material 624, the openings in the mesh being smaller than the size of the hydrogel pieces (e.g. beads) 650. This cylindrical-shaped cartridge is suitably sized for insertion into a mop handle that can be filled with water such as described in US2006/0280546; incorporated herein by reference.

The mop handle 640 is adapted on its lower end to receive a portion of a RTU cleaning solution dispensing assembly 660. The mop handle 640 is also adapted on its upper end to receive a portion of a reservoir assembly 610 that can be filled with water. The mop head 690 is coupled to the RTU cleaning solution dispensing assembly by means of a coupling joint 670. In the embodiment depicted, the fluid reservoir 630 is a bottle and the mop handle 640 comprises a hollow tube. In use, the water is conveyed from the reservoir assembly 610 to the floor via the hollow handle 640. As the water passes through the cartridge 620 containing the hydrogel cleaning concentrate a RTU cleaning solution is formed. This cleaning solution enters the fluid dispense assembly 660 exiting through the fluid dispense spout 655 to be deposited on the floor in proximity to the mop head 690. The fluid may then be spread about on the floor or any other surface in typical mopping fashion.

The hydrogel cleaning concentrate comprises a homogeneous mixture of a water insoluble polymer and polar solvent. The polar solvent of the hydrogel typically comprises water, a water-miscible organic solvent, or a mixture thereof. A water-miscible organic solvent refers to an organic solvent that is typically capable of hydrogen bonding and that forms a single phase solution when mixed with water. Suitable water-miscible organic solvents, which often contain hydroxyl or oxy groups, include alcohols, polyols having a weight average molecular weight no greater than about 300 g/mole, ethers, and polyethers having a weight average molecular weight no greater than about 300 g/mole. Exemplary water-miscible organic solvents include, but are not limited to, methanol, ethanol, isopropanol, n-propanol, ethylene glycol, triethylene glycol, glycerol, polyethylene glycol, propylene glycol, dipropylene glycol, polypropylene glycol, random and block copolymers of ethylene oxide and propylene oxide, dimethoxytetraglycol, butoxytriglycol, trimethylene glycol trimethyl ether, ethylene glycol dimethyl ether, ethylene glycol monobutyl ether, ethylene glycol monoethyl ether, and mixtures thereof.

The polar solvent is often present in the hydrogel at an amount greater than 10 weight percent based on a total weight of the precursor composition. In some exemplary precursor compositions, the polar solvent is present in an amount equal to at least 15 weight percent, at least 20 weight percent, at least 25 weight percent, at least 30 weight percent, at least 40 weight percent, or at least 50 weight percent based on the total weight of the precursor composition. The polar solvent in the precursor composition can be present in an amount up to 85 weight percent, up to 80 weight percent, up to 75 weight percent, up to 70 weight percent, or up to 60 weight percent based on the total weight of the precursor composition. In some precursor compositions, the polar solvent is present in an amount greater than 10 to 85 weight percent, greater than 10 to 80 weight percent, 20 to 80 weight percent, 30 to 80 weight percent, or 40 to 80 weight percent based on the total weight of the precursor composition.

In some embodiments, the cleaning concentrate comprises at least one surfactant as an active cleaning component. The term "surfactant", as used herein, is meant to mean and include a substance or compound that reduces surface tension when dissolved in water or water solutions, or that reduces interfacial tension between two liquids, or between a liquid and a solid. Surfactants generally contain both a hydrophilic group and a hydrophobic group.

The hydrogel cleaning concentrate may contain one or more surfactants selected from anionic, nonionic, cationic, ampholytic, amphoteric and zwitterionic surfactants and mixtures thereof. A surfactant that dissociates in water and releases cation and anion is termed ionic. When present, ampholytic, amphoteric and zwitterionic surfactants are generally used in combination with one or more anionic and/or nonionic surfactants.

The active cleaning component (e.g. surfactant(s)) are typically present in the hydrogel at a concentration of at least 1, 2, 3, 4, or 5 wt-% and more typically at least 6, 7, 8, 9, or 10 wt-%. Preferably, the concentration of active cleaning component (e.g. surfactant(s)) in the hydrogel is at least equivalent to the concentration of surfactant in the liquid cleaning concentrate the hydrogel can be used in place of. More preferably, the active cleaning component (e.g. surfactant(s)) in the hydrogel is significantly greater than the concentration of surfactant in the liquid cleaning concentrate the hydrogel can be used in place of. By providing a higher concentration of surfactant, a higher volume of diluted cleaning solution can be prepared from the hydrogel cleaning concentrate than an equivalent mass of liquid cleaning concentrate. In some embodiments, the hydrogel cleaning concentrate comprises greater than 15, 20, 25, or 30 wt-% solids of active cleaning component(s) such as mixtures of surfactants.

In some embodiments, the hydrogel cleaning concentrate comprises at least one cationic surfactant. Suitable cationic surfactants to be used herein include the quaternary ammonium surfactants. The quaternary ammonium surfactant may be a mono C6-C16, or a C6-C10 N-alkyl or alkenyl ammonium surfactant wherein the remaining N positions are substituted by methyl, hydroxyethyl or hydroxypropyl groups. Also suitable are mono-alkoxylated and bis-alkoxylated amine surfactants. Some species of quaternary ammonium compounds (e.g. mono C12-C16) may serve a dual purpose of acting as a surfactant and acting as an antimicrobial agent.

In some embodiments, the hydrogel cleaning concentrate comprises at least one nonionic surfactant. Nonionic surfactants have no ions. These chemicals derive their polarity from having a (e.g. oxygen-rich) polar portion of the molecule at one end and a large organic molecule (e.g. alkyl group containing from 6 to 30 carbon atoms) at the other end. The oxygen component is usually derived from short polymers of ethylene oxide or propylene oxide. Nonionic surfactants include for example alkyl polysaccharides, amine oxides, fatty alcohol ethoxylates, alkyl phenol ethoxylates, and ethylene oxide/propylene oxide block copolymers. Some nonionic surfactants such as alkyl pyrrolidinone and ethylene glycol monohexyl ether also reduce streaking on (e.g. glass) surfaces. Various nonionic surfactants are commercially available such as from Huntsman under the trade designation "Surfonic".

One preferred class of nonionic surfactant is alkyl polysaccharides having a hydrophobic group containing from 6 to 30 carbon atoms and a polysaccharide, e.g., a polyglycoside, hydrophilic group containing from 1.3 to 10 saccharide units. Alkylpolyglycosides may have the formula: $R^2O(C_nH_{2n}O)_t$ $(glycosyl)_x$ wherein $R^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 8. In some embodiments, $R^2$ is an alkyl group having 6 to 18 and more preferably 10 to 16 carbon atoms. The glycosyl may be derived from glucose. In some embodiments, the hydrogel cleaning concentrate may comprise a combination of an alkyl polyglycoside and alkyl pyrrolidone as described in WO2007/143344; incorporated herein by reference. Commercially available alkyl polysaccharides surfactant include "GLUCOPON" series non-ionic surfactants, commercially available from Cognis Corporation, Cincinnati, Ohio, such as a mixture of alkyl polyglycosides and cocoglucosides available under the trade designation "GLUCOPON 425 N" surfactant.

The surfactant may also comprise a nonionic fluorosurfactants, cationic fluorosurfactants, or mixture thereof that is soluble or dispersible in an aqueous based composition. Suitable nonionic fluorosurfactant compounds are commercially available from 3M under the trade designation "Fluorad" and from Dupont under the trade designation "Zonyl".

The hydrogel cleaning concentrate may comprise an anionic surfactant. Anionic surfactants include salts (e.g. sodium, potassium, ammonium, and substituted ammonium salts such as mono-, di- and tri-ethanolamine salts) of the anionic sulfate, sulfonate, carboxylate and sarcosinate surfactants. Anionic surfactants may comprise a sulfonate or a sulfate surfactant. Anionic surfactants may comprise an alkyl sulfate, a linear or branched alkyl benzene sulfonate, or an alkyldiphenyloxide disulfonate, as described herein. Acids and bases are commonly used as active cleaning components to react with various inorganic contaminants, especially hard water residues comprised of various inorganic oxides. When an acid or base is employed as the active cleaning component, the resulting RTU is typically not neutral (i.e. a pH of 6.5 to 7.5). When the hydrogel cleaning concentrate is acidic the resulting RTU typically has a pH of less than 6.5. The pH of the resulting RTU is typically at least 4 and no greater than about 6. When the hydrogel cleaning concentrate is basic the resulting RTU has a pH greater than 7.5. The pH of the resulting RTU is at least 8 and typically no greater than 10.

Any of a wide variety of acids can be used including for example phosphoric acid, sulfuric acid, nitric acid, hydrochloric acid, oxalic acid, boric acid, acetic acid (vinegar), citric acid, peracetic acid, tartaric acid, and the like. Likewise a wide variety of bases can be used such as sodium hydroxide, ammonium hydroxide, sodium bicarbonate, trisodium phosphate, and the like.

Enzymes are a class of proteins that catalyze a broad spectrum of reactions. Proteolytic enzymes are used as an active cleaning component to cleave the peptide bond of proteins with the simultaneous formation of water (hydrolysis). Lyase enzymes remove or add specific chemical groups. For example, cellulase decomposes cellulose to glucose. The enzymes for use in the hydrogel cleaning concentrate typically have a molecular weight of no greater than about 10,000 daltons. Following is a partial list of some of the enzymes that are commonly employed as an active cleaning component.

| | |
|---|---|
| Amylase | Starch hydrolysis |
| Alcalase | Converts proteins |
| Lipase or lipolase | Hydrolysis of fats |
| Protease | Hydrolysis of peptide linkages |

Enzymes suitable for use in cleaning concentrates are commercially available from Novozymes and Enzyme Solution Inc.

In some embodiments, the hydrogel cleaning concentrate comprises at least one biologically active agent including antimicrobial agents, disinfectants, antiseptics, antifungal agents, and antibacterial agents in combination with an active cleaning component such as a surfactant.

Any known antimicrobial agents that are compatible with the precursor compositions or the resulting hydrogels can be used. These include, but are not limited to, chlorhexidine salts such as chlorhexidine gluconate (CHG), parachlorometaxylenol (PCMX), triclosan, hexachlorophene, fatty acid monoesters and monoethers of glycerin and propylene glycol such as glycerol monolaurate, glycerol monocaprylate, glycerol monocaprate, propylene glycol monolaurate, propylene glycol monocaprylate, propylene glycol moncaprate, phenols, surfactants and polymers that include a (C12-C22) hydrophobe and a quaternary ammonium group or a protonated tertiary amino group, quaternary amino-containing compounds such as quaternary silanes and polyquaternary amines such as polyhexamethylene biguanide, silver containing compounds such as silver metal, silver salts such as silver chloride, silver oxide and silver sulfadiazine, methyl parabens, ethyl parabens, propyl parabens, butyl parabens, octenidene, 2-bromo-2-nitropropane-1,3 diol, or mixtures thereof. Other antimicrobial agents are described, for example, in U.S. Patent Application Publications 2006/0052452 (Scholz), 2006/0051385 (Scholz), and 2006/0051384 (Scholz).

Non-limiting examples of these quaternary ammonium compounds and phenolic antimicrobial agents include benzalkonium chlorides and/or substituted benzalkonium chlorides, di($C_6$-$C_{14}$)alkyl di short chain (C1-4 alkyl and/or hydroxyalkyl) quaternaryammonium salts, N-(3-chloroallyl) hexaminium chlorides, benzethonium chloride, methylbenzethonium chloride, and cetylpyridinium chloride. Other quaternary compounds include alkyl dimethylbenzylammonium chlorides, dialkylmethylbenzylammonium chlorides, and mixtures thereof.

Biguanide antimicrobial actives include for example polyhexamethylene biguanide hydrochloride, p-chlorophenyl biguanide, 4-chloro-benzhydryl biguanide, halogenated hexidine such as, but not limited to, chlorhexidine (1,1'-hexamethylene-bis-5-(4-chlorophenyl biguanide). Various other surfactant and antimicrobial agents are known such as described in U.S. Pat. No. 7,318,871 and US2007/0238634; incorporated herein by reference.

The hydrogel cleaning concentrates may optionally contain one or more adjuncts including for example stain and soil repellants, lubricants, odor control agents, perfumes, fragrances and fragrance release agents, and bleaching agents. Other adjuncts include, but are not limited to, acids, electrolytes, dyes and/or colorants, solubilizing materials, stabilizers, thickeners, defoamers, hydrotropes, cloud point modifiers, preservatives, and other polymers. The solubilizing materials, when used, include, but are not limited to, hydrotropes (e.g. water soluble salts of low molecular weight organic acids such as the sodium and/or potassium salts of toluene, cumene, and xylene sulfonic acid). The acids, when used, include, but are not limited to, organic hydroxy acids, citric acids, keto acid, and the like. Electrolytes, when used, include, calcium, sodium and potassium chloride. Defoamers, when used, include, but are not limited to, silicones, aminosilicones, silicone blends, and/or silicone/hydrocarbon blends. Bleaching agents, when used, include, but are not limited to, peracids, hypochlorite, and hydrogen peroxide, and/or sources of hydrogen peroxide. Preservatives, when used, include, but are not limited to, mildewstat or bacteriostat, methyl, ethyl and propyl parabens, short chain organic acids (e.g. acetic, lactic and/or glycolic acids), bisguanidine compounds (e.g. Dantagard and/or Glydant) and/or short chain alcohols (e.g. ethanol and/or IPA). The compositions may also optionally comprise an effective amount of a skin care agent such as a kerotolytic such as (2,5-iioxo-4-imidazolidinyl)urea also know as allantoin, for providing the function of encouraging healing of the skin. Other skin care agents include for example panthenol, bisabolol, ichthammol, stearyl glycyrrhetinate, ammonium glycyrrhetinate, vitamin E and/or A; and plant extracts such as from green tea, kola, oat, tea tree, and aloe; as well as skin moisteners; skin powders and the like.

The hydrogel cleaning concentrate according to the invention may optionally comprise pine oil, terpene derivatives or other essential oil for cleaning or antimicrobial efficacy as well as for deodorizing properties. Essential oils include, but are not limited to, those obtained from thyme, lemongrass, citrus, lemons, oranges, anise, clove, aniseed, pine, cinnamon, geranium, roses, mint, lavender, citronella, eucalyptus, peppermint, camphor, sandalwood, rosmarin, vervain, fleagrass, ratanhiae, cedar and mixtures thereof. When present, such oils are typically present in an amount of at least 0.01% by weight and no greater than about 5% by weight.

The hydrogel cleaning concentrate may further comprise an indicator such as a colorant. The hydrogel cleaning concentrate beads may become colorless as the active cleaning component diffuses into the cleaning solution. Conversely, the cleaning solution may become colored.

In some embodiments, the method or package of hydrogel cleaning concentrate may comprise a first mass comprising a first active cleaning component and a second mass comprising a different active cleaning component than the first mass. This aspect is particularly useful for combinations of active cleaning component that cannot ordinarily be combined in a single RTU cleaning solution such as when a first active cleaning component reducing the efficacy of a second cleaning component. For example, the method or package may comprise an acid or base as an active cleaning component in the first mass (e.g. of beads) and an enzyme such as protease and/or amylase in the second mass (e.g. of beads). Typically, enzymes are used as cleaners for organic contaminants such as food stains or grass stains on clothes, while an acid or base solution is used to clean inorganic dirt stains. For example Spray 'N Wash dual power product has two compartments, one containing the enzyme mixture and the second containing a citric acid composition. If the enzyme and acid are not kept separate until use, the acid will deactivate the enzyme.

In another embodiment, the method or package of hydrogel cleaning concentrate may comprise a first mass comprising a first active cleaning component and a second mass comprising an adjunct that would reduce the efficacy of or deactivate the first active cleaning component if combined in a RTU cleaning solution. For example, the first mass (e.g. of beads) may comprise a surfactant such as alkyl polyglucoside and the second mass (e.g. of beads) may comprise hydrogen peroxide as a disinfectant. If combined as a RTU cleaning composition, the surfactant would deactivate the hydrogen peroxide. However, by having these components in separate masses (e.g. two types of beads in a single nonwoven pouch package), the first and second hydrogel beads can be combined with water to make the RTU composition.

The polymerizable material of the hydrogel precursor is miscible with the polar solvent and does not phase separate from the polar solvent. As used herein with reference to the polymerizable material, the term "miscible" means that the polymerizable material is predominately soluble in the polar solvent or compatible with the polar solvent. However, there can be a small amount of the polymerizable material that does not dissolve in the polar solvent. For example, the polymerizable material may have an impurity that does not dissolve in the polar solvent. Generally, at least 95 weight percent, at least 97 weight percent, at least 98 weight percent, at least 99 weight percent, at least 99.5 weight percent, at least 99.8 weight percent, or at least 99.9 weight percent of the polymerizable material is soluble in the polar solvent.

As used herein, the term “polymerizable material” can refer to a monomer or to a mixture of monomers. The terms “monomer” and “monomer molecule” are used interchangeably to refer to a compound that contains at least one polymerizable group capable of free-radical polymerization. The polymerizable group is usually an ethylenically unsaturated group.

In some embodiments, the polymerizable material includes a monomer of a single chemical structure. In other embodiments, the polymerizable material includes a plurality of different monomers (i.e., there is a mixture of monomers having different chemical structures). Whether the polymerizable material includes one monomer or a mixture of monomers, the polymerizable material has an average number of polymerizable groups (e.g., ethylenically unsaturated groups) per monomer molecule equal to at least 1.2. The polymerizable material can include, for example, a single type of monomer that has two or more polymerizable groups. Alternatively, the polymerizable material can include a plurality of different types of monomers such that the average number of polymerizable groups per monomer molecule is equal to at least 1.2. In some embodiments, the average number of polymerizable groups per monomer molecule is equal to at least 1.3, at least 1.4, at least 1.5, at least 1.6, at least 1.7, at least 1.8, at least 1.9, at least 2.0, at least 2.1, at least 2.2, at least 2.3, at least 2.4, at least 2.5, at least 2.6, at least 2.7, at least 2.8, at least 2.9, or at least 3.0.

The precursor composition generally contains 25 to 90 weight percent polymerizable material based on the total weight of the precursor composition. For example, the precursor composition contains at least 25 weight percent, at least 30 weight percent, at least 40 weight percent, or at least 50 weight percent polymerizable material. The precursor composition can include up to 90 weight percent, up to 80 weight percent, up to 75 weight percent, up to 70 weight percent, or up to 60 weight percent polymerizable material. In some precursor compositions, the amount of polymerizable material is in the range of 25 to 90 weight percent, 30 to 90 weight percent, 40 to 90 weight percent, or 40 to 80 weight percent based on the total weight of the precursor composition.

The polymerizable material often includes one or more (meth)acrylates. As used herein, the term “(meth)acrylate” refers to a methacrylate, acrylate, or mixture thereof. The (meth)acrylate contains a (meth)acryloyl group. The term “(meth)acryloyl” refers to a monovalent group of formula $H_2C{=}CR^b$—(CO)— where $R^b$ is hydrogen or methyl and (CO) denotes that the carbon is attached to the oxygen with a double bond. The (meth)acryloyl group is the polymerizable group (i.e., the ethylenically unsaturated group) of the (meth)acrylate that is capable of free-radical polymerization. All the polymerizable materials can be (meth)acrylates or the polymerizable materials can include one or more (meth)acrylates in combination with other monomers that have ethylenically unsaturated groups.

In many embodiments, the polymerizable material includes a poly(alkylene oxide (meth)acrylate). The terms poly(alkylene oxide (meth)acrylate), poly(alkylene glycol (meth)acrylate), alkoxylated (meth)acrylate, and alkoxylated poly(meth)acrylate can be used interchangeably to refer to a (meth)acrylate having at least one group that contains two or more alkylene oxide residue units (also referred to as alkylene oxide units). There are often at least 5 alkylene oxide residue units. The alkylene oxide unit is a divalent group of formula —OR— where R is an alkylene having up to 10 carbon atoms, up to 8 carbon atoms, up to 6 carbon atoms, or up to 4 carbon atoms. The alkylene oxide units are often selected from ethylene oxide units, propylene oxide units, butylene oxide units, or mixtures thereof.

As long as the average number of ethylenically unsaturated groups (e.g., (meth)acryloyl groups) per monomer molecule is equal to at least 1.2, the polymerizable material can include a single (meth)acrylate or a mixture of (meth)acrylates. Specific examples of suitable polymerizable materials with one ethylenically unsaturated group per monomer molecule include, but are not limited to, 2-hydroxyethyl (meth)acrylate, 2-hydroxypropyl (meth)acrylate, 3-hydroxypropyl (meth)acrylate, 4-hydroxybutyl (meth)acrylate, (meth)acrylonitrile, (meth)acrylamide, caprolactone (meth)acrylate, poly(alkylene oxide (meth)acrylate) (e.g., poly(ethylene oxide (meth)acrylate), poly(propylene oxide (meth)acrylate), and poly(ethylene oxide-co-propylene oxide (meth)acrylate)), alkoxy poly(alkylene oxide (meth)acrylate), (meth) acrylic acid, β-carboxyethyl (meth)acrylate, tetrahydrofurfuryl (meth)acrylate, N-vinyl pyrrolidone, N-vinylcaprolactam, N-alkyl(meth)acrylamide (e.g., N-methyl(meth)acrylamide), and N,N-dialkyl(meth)acrylamide (e.g., N,N-dimethyl(meth)acrylamide).

Suitable polymerizable materials with two ethylenically unsaturated groups per monomer molecule include, for example, alkoxylated di(meth)acrylates. Examples of alkoxylated di(meth)acrylates include, but are not limited to, poly(alkylene oxide di(meth)acrylates) such as poly(ethylene oxide di(meth)acrylates) and poly(propylene oxide di(meth) acrylates); alkoxylated diol di(meth)acrylates such as ethoxylated butanediol di(meth)acrylates, propoxylated butanediol di(meth)acrylates, and ethoxylated hexanediol di(meth)acrylates; alkoxylated trimethylolpropane di(meth)acrylates such as ethoxylated trimethylolpropane di(meth)acrylate and propoxylated trimethylolpropane di(meth)acrylate; and alkoxylated pentaerythritol di(meth)acrylates such as ethoxylated pentaerythritol di(meth)acrylate and propoxylated pentaerythritol di(meth)acrylate.

Examples of suitable polymerizable materials with three ethylenically unsaturated groups per monomer molecule include, for example, alkoxylated tri(meth)acrylates. Examples of alkoxylated tri(meth)acrylates include, but are not limited to, alkoxylated trimethylolpropane tri(meth)acrylates such as ethoxylated trimethylolpropane tri(meth)acrylates, propoxylated trimethylolpropane tri(meth)acrylates, and ethylene oxide/propylene oxide copolymer trimethylolpropane tri(meth)acrylates; and alkoxylated pentaerythritol tri(meth)acrylates such as ethoxylated pentaerythritol tri (meth)acrylates.

Suitable polymerizable materials with at least four ethylenically unsaturated groups per monomer include, for example, alkoxylated tetra(meth)acrylates and alkoxylated penta(meth)acrylates. Examples of alkoxylated tetra(meth) acrylates include alkoxylated pentaerythritol tetra(meth) acrylates such as ethoxylated pentaerythritol tetra(meth) acrylates.

In some embodiments, the polymerizable material includes a poly(alkylene oxide (meth)acrylate) having at least 2 (meth)acryloyl groups per monomer molecule. The alkoxylated portion (i.e., the poly(alkylene oxide) portion) often has at least 5 alkylene oxide units selected from ethylene oxide units, propylene oxide units, butylene oxide units, or a combination thereof. That is, each mole of the poly(alkylene oxide (meth)acrylate) contains at least 5 moles of alkylene oxide units. The plurality of alkylene oxide units facilitates the solubility of the poly(alkylene oxide (meth)acrylate) in the polar solvent. Some exemplary poly(alkylene oxide (meth)acrylates) contain at least 6 alkylene oxide units, at least 8 alkylene oxide units, at least 10 alkylene oxide units, at least 12 alkylene oxide units, at least 15 alkylene oxide units, at least 20 alkylene oxide units, or at least 30 alkylene oxide units. The poly(alkylene oxide (meth)acrylate) can contain poly(alkylene oxide) chains that are homopolymer chains, block copolymer chains, random copolymer chains, or mixtures thereof. In some embodiments, the poly(alkylene oxide) chains are poly(ethylene oxide) chains.

Any molecular weight of this poly(alkylene oxide (meth) acrylate) having at least 2 (meth)acryloyl groups can be used as long as the desired physical form (e.g. polymeric beads, fibers, or molded shapes) can be formed from the precursor composition. The weight average molecular weight of this poly(alkylene oxide (meth)acrylate) is often no greater than 2000 g/mole, no greater than 1800 g/mole, no greater than 1600 g/mole, no greater than 1400 g/mole, no greater than 1200 g/mole, or no greater than 1000 g/mole. In other applications, however, it is desirable to include a poly(alkylene oxide (meth)acrylate) in the polymerizable material that has a weight average molecular weight greater than 2000 g/mole.

The preparation of some exemplary poly(alkylene oxide (meth)acrylates) having multiple (meth)acryloyl groups are described in U.S. Pat. No. 7,005,143 (Abuelyaman et al.) as well as in U.S. Patent Application Publication Nos. 2005/0215752 A1 (Popp et al.), 2006/0212011 A1 (Popp et al.), and 2006/0235141 A1 (Riegel et al.). Suitable poly(alkylene oxide (meth)acrylates) having an average (meth)acryloyl functionality per monomer molecule equal to at least 2 and having at least 5 alkylene oxide units are commercially available, for example, from Sartomer (Exton, Pa.) under the trade designations "SR9035" (ethoxylated (15) trimethylolpropane triacrylate), "SR499" (ethoxylated (6) trimethylolpropane triacrylate), "SR502" (ethoxylated (9) trimethylolpropane triacrylate), "SR415" (ethoxylated (20) trimethylolpropane triacrylate), and "CD501" (propoxylated (6) trimethylolpropane triacrylate) and "CD9038" (ethoxylated (30) bis-phenol A diacrylate). The number in parentheses refers to the average number of alkylene oxide units per monomer molecule. Other suitable poly(alkylene oxide (meth)acrylates) include polyalkoxylated trimethylolpropane triacrylates such as those commercially available from BASF (Ludwigshafen, Germany) under the trade designation "LAROMER" with at least 30 alkylene oxide units.

Some exemplary precursor compositions contain a poly (alkylene oxide (meth)acrylate) having at least 2 (meth)acryloyl groups per monomer molecule, having at least 5 ethylene oxide units, and having a weight average molecular weight less than 2000 g/mole. An even more specific exemplary precursor composition can include an ethoxylated trimethylolpropane triacrylate having a weight average molecular weight less than 2000 g/mole. Often the ethoxylated trimethylolpropane triacrylate contains impurities having one (meth)acryloyl group, two (meth)acryloyl groups, or mixtures thereof. For example, commercially available "SR415" (ethoxylated (20) trimethylolpropane triacrylate), often has an average functionality per monomer molecule less than 3 (when analyzed, the average functionality per monomer molecule was about 2.5). Although impurities may be present, the average functionality per monomer molecule in the precursor composition is equal to at least 1.2.

In addition to the poly(alkylene oxide (meth)acrylate) having at least 2 (meth)acryloyl groups per monomer molecule, the precursor composition can include other monomers that are added to impart certain characteristics to the hydrogel cleaning concentrate. In some instances, the precursor composition can contain an anionic or cationic monomer, such as described in WO 20007/146722 incorporated herein by reference.

Some exemplary polymerizable materials contain only nonionic monomers. That is, the polymerizable material is substantially free of both anionic monomers and cationic monomers. As used herein with reference to the anionic or cationic monomers, "substantially free" means that the polymerizable material contains less than 1 weight percent, less than 0.5 weight percent, less than 0.2 weight percent, or less than 0.1 weight percent anionic monomer or cationic monomer based on the weight of the polymerizable material.

In some embodiments, the precursor compositions contain up to 20 weight percent anionic monomer based on the total weight of polymerizable material in the precursor composition, wherein the anionic monomer has an ethylenically unsaturated group in addition to an acidic group, a salt of an acidic group, or a mixture thereof.

Although cationic monomers such as those having a quaternary amino group, can impart antimicrobial properties to the hydrogel, once polymerized into the hydrogel such cationic monomers are no longer able to diffuse out of the hydrogel to form an antimicrobial cleaning solution.

In addition to the polar solvent and the polymerizable material, the precursor composition can include one or more optional additives such as processing agents such as described in WO 2007/146722.

One exemplary processing agent is an initiator. Most precursor compositions include an initiator for the free-radical polymerization reaction. The initiator can be a photoinitiator, a thermal initiator, or a redox couple. The initiator can be either soluble in the precursor composition or dispersed in the precursor composition.

An example of a suitable soluble photoinitiator is 2-hydroxy-1-[4-(2-hydroxyethoxy)phenyl]-2-methyl-1-propanone, which is commercially available under the trade designation "IRGACURE 2959" from Ciba Specialty Chemicals (Tarrytown, N.Y.). An example of a suitable dispersed photoinitiator is alpha, alpha-dimethoxy-alpha-phenylacetophenone, which is commercially available under the trade designation "IRGACURE 651" from Ciba Specialty Chemicals. Other suitable photoinitiators are the acrylamidoacetyl photoinitiators, described in U.S. Pat. No. 5,506,279, that contain a polymerizable group as well as a group that can function as an initiator. The initiator is usually not a redox initiator as used in some polymerizable compositions known in the art. Such initiators could react with bioactive agents, if present.

The method of forming polymeric beads can include providing a precursor composition and forming droplets of the precursor composition that are totally surrounded by a gas phase such as described in WO 2007/146722. The method further includes exposing the droplets to radiation for a time sufficient to at least partially polymerize the polymerizable material in the precursor composition and to form a first swollen polymeric bead. The droplets can fall under the force of gravity past a radiation source or can be blown (e.g. upward) as a spray.

When the hydrogel precursor composition comprises a relatively high concentration of surfactant the surface energy of the precursor can be reduced to no greater than 30 mN/m. It is surprising that such a low surface energy precursor will still form droplets.

For a given method of droplet formation, the particle size distribution may be broad or narrow. Narrow particle size distributions can be monodisperse or nearly monodisperse. As an example, when ultrasonic atomization is used to generate liquid droplets, a mean diameter of approximately 50 micrometers may be obtained but the bead size distribution may range from about 1 micrometer to about 100 micrometers. Other droplet formation techniques will provide different bead size distributions. For applications where a narrow size distribution of beads is desired, more controlled drop formation methods may be used or additional post-process screening can be done to narrow the size distribution, as is known to those skilled in the art.

The polymer beads can have a wide variety of sizes. The diameter of the beads depends on the exact method used to generate the liquid droplets of the precursor composition prior to radiation curing and can range from less than one micrometer to several thousand micrometers. Particularly suitable bead diameters are in the range of 1 to about 5000 micrometers, in the range of 1 to 4000 micrometers, in the range of 10 to 3500 micrometers, or in the range of 100 to 2000 micrometers.

Upon exposure to radiation, the polymerizable material within the precursor composition undergoes a free-radical polymerization reaction. As used herein, the term "radiation" refers to actinic radiation (e.g., radiation having a wavelength in the ultraviolet or visible region of the spectrum), accelerated particles (e.g., electron beam radiation), thermal (e.g., heat or infrared radiation), or the like. The radiation is often actinic radiation or accelerated particles, because these energy sources tend to provide good control over the initiation and rate of polymerization. Additionally, actinic radiation and accelerated particles can be used for curing at relatively low temperatures. This avoids degrading components that might be sensitive to the relatively high temperatures that might be required to initiate the polymerization reaction with thermal radiation. Any suitable actinic radiation sources that can produce energy in the desired region of the electromagnetic spectrum can be used. Exemplary sources of actinic radiation include mercury lamps, xenon lamps, carbon arc lamps, tungsten filament lamps, lasers, sunlight, and the like.

The invention is further described with reference to the following non-limiting examples.

Cleaning Concentrate No. 1

| Component | Chemical Decription (Trade Designation, Supplier) | Wt-% |
|---|---|---|
| Polar solvent | D.I. Water | 59.56 |
| Nonionic Surfactant | mixture of alkyl polyglycosides and cocoglucosides (Glucopon 425N, Cognis) | 36.00 |
| Surfactant | organic polymer blend (Easy Wet 20, International Specialty Products) | 3.70 |
| Colorant | (C.I. Solvent Green 7 Dye) | 0.02 |
| Essential Oil | (Belle Air Fragrance #36519 Citrus) | 0.27 |
| Defoamer | (Ultra Additives Foam Ban MS575) | 0.30 |
| Defoamer | (Cognis Dehydran 1620) | 0.15 |

3M ™ Neutral Quat Disinfectant Cleaner Concentrate (Product No. 23 Twist 'n Fill ™ System)

| Generic Chemical Description | Ingredients | Wt-% |
|---|---|---|
| Polar solvent | Water | 60-90 |
| Antimicrobial | Didecyl dimethyl (C22) ammonium chloride | 10.14 |
| Antimicrobial | N-alkyl dimethylbenzyl ammonium chloride | 6.76 |
| Surfactant | Octyldimethlamine oxide | 1-5 |
| Adjunct | Ethylenediaminetetraacetic acid | 1-5 |
| Polar Solvent | Ethyl alcohol | 1-5 |
| Adjunct | Sodium hydroxide | 0-1.5 |

3M ™ 3-in-1 Floor Cleaner Concentrate (Product No. 24 Twist 'n Fill ™ System)

| Generic Chemical Description | Ingredients | Wt-% |
|---|---|---|
| Polar solvent | Water | 5-10 |
| Surfactant | Polyoxyethylene tridecyl ether | 30-70 |
| Polar Solvent | 2-ethyl-hexyloxyethanol | 10-30 |
| Surfactant | Octyldimethlamine oxide | 1-5 |
| Surfactant | Diethylene glycol mono(2-ethylhexy) ether | 1-5 |
| Adjunct | Fragrance | 0.5-1.5 |

3M ™ Bathroom Disinfectant Cleaner (Concentrate) (Product No. 4 Twist 'n Fill ™ System)

| Generic Chemical Description | Ingredients | Wt-% |
|---|---|---|
| Polar solvent | Water | 10-30 |
| Surfactant | 1-octyl-2-pyrrolidinone | 10-30 |
| Acid | Hydroxyacetic acid | 10-30 |
| Acid | Malic acid | 10-30 |
| Surfactant | Amines, coco alkyldimethyl, N-oxides | 1-5 |
| Fragrance | | <3 |
| Antimicrobial | Benzyl-C12-16-alkyldimethyl ammonium chloride | 2.00 |
| Antimicrobial | Octyldecyldimethyl ammonium chloride | 1.50 |
| Antimicrobial | Didecyl dimethyl ammonium chloride | 0.90 |
| Antimicrobial | Dioctyl dimethyl ammonium chloride | 0.60 |
| Polar Solvent | Ethyl alcohol | 0.5-1.5 |
| Acid | Methoxyacetic acid | 0.1-1 |

3M ™ Neutral Cleaner LO Concentrate (Product No. 33 Twist 'n Fill ™ System)

| Component | Chemical Decription Trade Designation, Supplier) | Wt-% |
|---|---|---|
| Polar solvent | Water | 60-90 |
| Non-ionic Surfactant | | 10-40 |
| Surfactant | | 1-5 |
| Surfactant | 1-octyl-2-pyrrolidinone | 0.1-1.0 |
| Polar Solvent | 1-undecanol | 0.1-1.0 |

Cleaning Concentrate No. 2

| Component | Chemical Decription Trade Designation, Supplier) | Wt-% |
|---|---|---|
| Polar solvent | D.I. Water | 30-60 wt-% |
| Acid | Acetic acid | 15-20 |
| Acid | Peroxyacetic acid | 15 |
| Disinfectant | Hydrogen Peroxide | 22 |

Example 1

Hydrogel Cleaning Concentrate Formed by Hydrogel Sorption of Cleaning Concentrate A homogeneous precursor composition was prepared by mixing 40 grams of 20-mole ethoxylated trimethylolpropane triacrylate (TMPTA) having a surface tension of 41.8 mN/m (SR415 from Sartomer, Exeter, Pa.), 60 grams deionized (DI) water, and 0.8 grams photoinitiator (IRGACURE 2959 from Ciba Specialty Chemicals, Tarrytown, N.Y.). The average functionality of the ethoxylated TMPTA used in this example and all subsequent examples was determined from HPLC data showing that the monomer was 53.6 weight percent trifunctional acrylate (52.5 mole percent), 45.3 weight percent difunctional acrylate (46.5 mole percent), and 1.0 weight percent monofunctional acrylate (1.1 mole percent). Using this information and assuming an average of 20-mole ethoxylation for each species, the average functionality was calculated to be about 2.5.

Beads were prepared from the precursor composition as described in Example 1 of WO 2007/146722. The beads ranged in diameter from approximately 1 millimeter to 4 millimeters.

The hydrogel beads were dried in a 70° C. oven for 2 hours. 5 grams of dried beads were combined with 10 grams of Cleaning Concentrate No. 1 and allowed to absorb for 2 hours. The beads were strained, rinsed and lightly dried using paper towels. The final weight of the beads after cleaner absorption was 10 grams indicating that 5 grams of the cleaner was absorbed into the beads. Since Cleaning Concentrate 1 had 36 wt-% Glucopan 425N and Glucopan 425N comprises 50 wt-% surfactant, the concentration of surfactant in the resulting hydrogel cleaning concentrate beads was 9 wt-%.

Twenty of the hydrogel cleaning concentrate beads (weighing 0.23 grams) were placed in a 100 ml burette. With the spigot closed, distilled water was added to the 70 ml mark. The spigot knob was turned until the rate of flow corresponded to 0.1 ml/sec.

Samples of the solution coming out of the burette were collected at fixed time intervals (4 ml samples were collected every minute of flow), and the appearance of the samples was observed. All samples were light yellow in color, and the color strength of the samples was the same indicating qualitatively a steady state diffusion of the cleaner into the flowing water.

Example 2

Hydrogel Cleaning Concentrate Formed by In-Situ Bead Formation with Liquid Cleaning Concentrate A hydrogel precursor solution was prepared by blending 80 g of 20-mole ethoxylated TMPTA (SR 415 available from Sartomer, Exeter, Pa.) with 120 g of the Cleaning Concentrate No. 1. To this was added 0.8 g Irgacure 2959 photoinitiator (Ciba Specialty Chemicals, Tarrytown, N.Y.). Once the photoinitiator had dissolved, beads were prepared in the same manner as Example 1 of WO 2007/146722 except that the orifice was positioned at the entrance of the quartz tube 20 inches above the UV zone.

Examples 3-6

Hydrogel Cleaning Concentrate Formed by In-Situ Bead Formation with Other Liquid Cleaning Concentrates Hydrogel cleaning concentrate beads were made according to the process of Example 2 using the following precursor compositions.

Concentration of Surfactant in Beads

| | | |
|---|---|---|
| Example 3: | 40 wt-% SR415<br>60 wt-% Product No. 23<br>1 wt-% photoinitiator | 0.6-3 wt-% |
| Example 4: | 40 wt-% SR415<br>60 wt-% Product No. 24<br>1 wt-% photoinitiator | 19.2-48 wt-% |
| Example 5: | 40 wt-% SR415<br>60 wt-% Product No. 4<br>1 wt-% photoinitiator | 12-36 wt-% acid<br>6.6-21 wt-% surfactant<br>18.6-57 wt-% active cleaning components |
| Example 6: | 40 wt-% SR415<br>60 wt-% Product No. 33<br>1 wt-% photoinitiator | 6.7-27.6 wt-% |

Example 7

Quantitative Assessment of Color for Dynamic Dilution of Hydrogel

To model dynamically combining water with a hydrogel cleaning concentrate a buret was filled with 5.009 g of the hydrogel cleaning concentrate beads of Example 4 (containing Product No. 24) and 25 mL water. The timer was started and every 2 minutes 5 mL were dispensed from the buret into separate bottles until 5 samples had been collected (Run 1). Then the beads were left in the buret and 25 mL water was added. The procedure was repeated until 5 more samples had been taken (Run 2). The target dilution factor for the cleaning concentrate is 250 to 400 (water) to 1. The following results demonstrate that the cleaning solution formed from the water passing through the beads in the burette exhibited the target concentration for both the first and second run.

HPLC Results:

| Time in Buret (min) | Average Dilution Factor |
|---|---|
| Run 1 | |
| 2 | 269 |
| 4 | 333 |
| 6 | 382 |
| 8 | 428 |
| 10 | 418 |
| Run 2 | |
| 2 | 199 |
| 4 | 300 |
| 6 | 341 |
| 8 | 341 |
| 10 | 309 |

Example 8

Quaternary Ammonium Compound Release Rate of Hydrogel

To model statically combining water with a hydrogel cleaning concentrate, 5 g of the hydrogel cleaning concentrate of Example 3 (containing Product No. 23) was combined with in 100 mL water. At 5 minute intervals 10 mL of liquid was removed and the concentration of quaternary ammonium antimicrobial compound (QAC) was tested with QAC Test Kit (commercially available from LaMotte). The concentration of QAC was then recalculated to account for removing 10 mL each time. [Corrected Concentration=(measured concentration)*(remaining volume)/100 mL]. The average diffusion rate (i.e. the slope) was calculated to be 20.8 ppm/min. After 20 minutes the liquid was light green. It is presumed that the surfactant diffuses at the same rate as the antimicrobial.

| Time (min) | Measured QAC Concentration (ppm) | Corrected QAC Concentration (ppm) |
|---|---|---|
| 5 | 210 | 210 |
| 10 | 340 | 306 |
| 15 | 530 | 424 |
| 20 | 740 | 518 |

Example 9

Effect of Surface Area on Hydrogel Cleaning Concentrate Release Rate

Example 8 was repeated except that prior to combining the hydrogel cleaning concentrate beads with water, the beads were crushed in a mortar and ground to a wet powdery consistency with the pestle. The concentration of QAC was then recalculated to account for removing 10 mL each time. (Corrected Concentration=(measured concentration)*(remaining volume)/100 mL). The average diffusion rate (i.e. the slope) was calculated to be 50.3 ppm/min. After 20 minutes the liquid was intense fluorescent green. It is presumed that the surfactant diffuses at the same rate as the antimicrobial.

| Crushed Hydrogel Cleaning Concentrate - QAC Release Rate | | |
|---|---|---|
| Time (min) | Measured QAC concentration (ppm) | Corrected QAC concentration (ppm) |
| 5 | 2660 | 2660 |
| 10 | 3560 | 3204 |
| 15 | 4000 | 3200 |
| 20 | 5000 | 3500 |

Example 10

Hydrogel Cleaning Concentrate Formed by In-Situ Bead Formation with Liquid Cleaning Concentrate and Sorption of Cleaning Concentrate 15 g of the hydrogel cleaning concentrate beads of Example 3 (containing Product No. 23) were dried in oven at 60° C. for 2 hours. The hydrogel beads were removed from the oven, weighed, and soaked in Product No. 23 for at least 3 hours to absorb the concentrate in an amount of about 2 times the weight of the dried hydrogel beads. The beads were filtered and dried with a paper towel. The beads were weighed to confirm the mass of absorbed Product No. 23. The sorption procedure, (i.e. drying and soaking) was repeated three times. The amount of antimicrobial available was calculated using the measured weights and the known concentration of antimicrobial in the Product No. 23.

| Results | |
|---|---|
| # of Reloading Cycles | Antimicrobial Concentration in Beads |
| 0 | *10.14 wt-% |
| 1 | 17.16 wt-% |
| 2 | 27.03 wt-% |
| 3 | 40.77 wt-% |

(*concentration of antimicrobial in Product No. 23 (10.14 + 6.76)) multiplied by (wt-% percentage of Product No. 23 in the beads (0.60))

Example 11

Instantaneous Formation of Ready to Use ("RTU") Cleaning Solution 0.5 grams of the hydrogel cleaning concentrate beads of Example 5 (containing Product No. 4) were combined with 20 grams of water. The pH of the water was 7.2 before adding the beads. Immediately after adding the beads, the pH dropped to 2.5 (due to the acid active components). The pH remained 2.5 after 10 minutes, indicating that most of the acid in the beads had diffused out immediately.

Example 12

Package of Hydrogel Cleaning Concentrate

Determining the Mass of Hydrogel for a Premeasured Package:

The recommended dilution for commercially available liquid cleaning concentrates, such as Product No. 23, Product No. 4, Product No. 33, is published in the literature. The target water to cleaning concentrate ratio for Product No. 4 liquid cleaning concentrate is 51:1. Since the hydrogel beads of Example 5 contain 60 wt-% cleaning concentrate, 3.3 g of beads corresponds to 1.98 g of cleaning concentrate which is the proper mass for dilution with 100 grams of water.

The recommended dilution for Product No. 23 liquid cleaning concentrate is 227:1. A pouch containing 2.4 grams of the hydrogel cleaning concentrate beads of Example 3 would contain 0.6×2.4=1.44 grams of concentrated cleaner, enough cleaner to produce 328 grams of RTU cleaning solution.

The recommended dilution for both Product No. 33 and Product No. 24 liquid cleaning concentrates is 200:1. Accordingly, 5 grams of hydrogel cleaning concentrate beads is the proper mass for dilution with 600 grams of water.

Process of Making Packaged Hydrogel Beads:

Various nonwoven materials were found to be suitable for making heat sealed enclosures to contain the hydrogel cleaning concentrate beads including spunbond polypropylene (20 grams/$m^2$), spunbond polyester (15 grams/$m^2$), both commercially available from BBA Fiberweb (Old Hickory, Tenn.), and spunbond nylon (17 grams/$m^2$) nonwoven commercially available from Cerex Advanced Fabrics, Inc (Pensacola, Fla.).

A sheet of non-woven material (about 6 inches wide) was folded in half and then perpendicular to the fold, two seals were made about 2" apart using an Audion Elektro Packaging Heat Sealer by Packaging Aids Corporation. If the nonwoven did not seal after one press of the heat sealer, the time was adjusted or multiple presses were used until sealed.

3.3 g of the hydrogel beads of Example 5 were poured into the opening (that was parallel to the fold) in the pouch and then the top opening was sealed shut using the same heat sealing method as above. The sealed pouch was about 2"×2".

Example 13

Hydrogel Cleaning Concentrate Comprising Acid as Active Component

Hydrogel cleaning concentrate beads were prepared as described in Example 1 except that beads were combined with vinegar instead of Cleaning Concentrate 1 for at least 3 hours. It was determined that the dried beads had sorbed 60 wt-% vinegar.

Example 14

Pouch of Hydrogel Cleaning Concentrate Comprising Hydrogel Beads Comprising Acid as Active Component 5.5 g of the vinegar-containing hydrogels of Example 13 were rinsed with distilled water twice and dried on a paper towel. 2.508 g were then combined with 1.904 g baking soda in a nonwoven enclosure as described in Example 12. This pouch was added to a bottle containing 100 mL water. Bubbles formed inside the pouch within a minute and continued to form for several hours as a result of the $CO_2$ gas generated as a result of the acid-base reaction between vinegar and baking soda. Another pouch having the same contents sat on the bench top for several days. During that time, there were no signs of such acid-base reaction.

Example 15

Hydrogel Beads Comprising Acid as Active Component and an Antiseptic

Hydrogel cleaning concentrate beads were prepared in the same manner as Example 1 except that the beads were combined with Cleaning Concentrate 2 instead of Cleaning Concentrate 1.

Example 16

Hydrogel Beads Comprising Surfactant as Active Component

Hydrogel cleaning concentrate beads were prepared in the same manner as Example 1 except that the beads were combined with Glucopan 425N instead of Cleaning Concentrate 1.

Example 17

Pouch of Hydrogel Cleaning Concentrate Comprising Hydrogel Beads of Example 15 in Combination with Hydrogel Beads of Example 16

0.29 g of the hydrogel cleaning concentrate beads of Example 16 and 1.00 g of the hydrogel cleaning concentrate beads of Example 15.

The pouch from Example 17 was combined with 70.03 g of water.

1.00 g of the hydrogel cleaning concentrate beads of Example 15 were combined with 70.06 g water.

For the Control, 0.5 g of Cleaning Concentrate 2 was combined with 70.06 g of water.

Peroxide concentration in the solution was measured using high level peroxide test strips commercially available from Indigo Instruments.

| Peroxide Concentration (g/L) | | | |
|---|---|---|---|
| Time (hrs:min) | Control | Peroxide Hydrogels | Peroxide/Glucopon 425N Hydrogels |
| 0:00 | | 1.0 | 1.0 |
| 0:15 | 1.0 | | |
| 1:00 | 1.0 | 1.5 | 1.0 |
| 2:00 | 1.0 | 1.5 | 1.5 |
| 4:30 | 1.0 | 1.5 | 1.5 |
| 7:00 | 1.0 | 1.0 | 1.0 |
| 23:00 | 1.0 | 1.0 | 1.0 |
| 27:00 | 0.8 | 1.0 | 1.0 |
| 31:00 | 0.8 | 1.0 | 1.0 |
| 48:00 | 0.8 | 1.0 | 1.0 |

The results show that incorporating the hydrogen peroxide into the hydrogels prevented the peroxide concentration from decreasing below 1.0 g/L as it did for the control. The results also show that that the Glucopon 425N did not deactivate the hydrogen peroxide of Cleaning Concentrate 2 within 48 hours.

What is claimed is:

1. A method of making a cleaning solution comprising:

providing a mass of a hydrogel cleaning concentrate wherein the mass of hydrogel cleaning concentrate is provided as a plurality of discrete free-flowing pieces ranging in size from about 0.5 mm to 5 mm or a unitary mass having larger dimensions than the pieces, the mass of hydrogel cleaning concentrate comprising an active cleaning component and a homogeneous mixture of a water insoluble polymer comprising crosslinked poly (alkylene)oxide (meth)acrylate units and polar solvent;

combining the hydrogel cleaning concentrate with water in an amount of at least 10 times the mass of hydrogel cleaning concentrate to form a cleaning solution; and separating the insoluble polymer from the cleaning solution.

2. The method of claim 1 wherein the active cleaning component is selected from the group consisting of a surfactant, an acid, a base, an enzyme and mixtures thereof.

3. The method of claim 1 wherein the mass of hydrogel cleaning concentrate and water are combined in a receptacle and the receptacle comprises a means for separating the insoluble polymer from the cleaning solution.

4. The method of claim 3 wherein the receptacle is a gravity-fed receptacle that attaches to a water dispensing system.

5. The method of claim 1 wherein the mass of hydrogel cleaning concentrate is contained within a water permeable and water insoluble enclosure and the enclosure is combined with the water.

6. The method of claim 5 wherein the enclosure comprises a nonwoven material.

7. The method of claim 5 wherein the enclosure comprises a refillable cartridge.

8. The method of claim 1 wherein the cleaning solution reaches a ready to use concentration in less than 15 minutes.

9. The method of claim 1 wherein the cleaning solution reaches a ready to use concentration in less than 1 minute.

10. The method of claim 1 wherein the water insoluble polymer further comprises photoinitiator.

11. The method of claim 1 wherein the discrete pieces are beads, fibers, or particles.

12. The method of claim 5 wherein the enclosure comprises a first hydrogel cleaning concentrate mass comprising a first active cleaning component and a second hydrogel cleaning concentrate mass comprising a different active cleaning component than the first hydrogel cleaning concentrate mass.

13. The method of claim 1 wherein the hydrogel cleaning concentrate is separated from the cleaning solution and recombined with water to form a second cleaning solution.

14. The method of claim 1 wherein the water is statically combined with the cleaning concentrate.

15. The method of claim 1 wherein the water is dynamically combined with the concentrate.

16. The method of claim 1 wherein the mass of hydrogel cleaning concentrate is combined with water in an amount ranging from 50 to 500 times the mass of the hydrogel cleaning concentrate.

17. The method of claim 1 wherein the mass of hydrogel cleaning concentrate comprises about 25 wt-% to 70 wt-% of the water insoluble polymer and 15 wt-% to 75 wt-% of the polar solvent.

18. The method of claim 1 wherein the mass of hydrogel cleaning concentrate comprises at least 5 wt-% of surfactant.

19. The method of claim 18 wherein the polar solvent in combination with the surfactant has a surface energy of no greater than 30 mN/m.

20. The method of claim 1 wherein the mass of hydrogel cleaning concentrate further comprises an antimicrobial agent, fragrance, or combination thereof.

21. The method of claim 1 wherein the water insoluble polymer does not become a component of the cleaning solution.

22. The method of claim 1 wherein the mass of hydrogel cleaning concentrate provides a means for dry delivery of liquid cleaning concentrates.

23. The method of claim 1 wherein the mass of hydrogel cleaning concentrate feels dry to the touch.

* * * * *

UNITED STATES PATENT AND TRADEMARK OFFICE

CERTIFICATE OF CORRECTION

PATENT NO. : 8,846,595 B2
APPLICATION NO. : 12/992139
DATED : September 30, 2014
INVENTOR(S) : Ylitalo et al.

It is certified that error appears in the above-identified patent and that said Letters Patent is hereby corrected as shown below:

In the Specification

Column 11
Line 9, delete "moncaprate," and insert -- monocaprate, --, therefor.

Line 18, delete "octenidene," and insert -- octenidine, --, therefor.

Line 64, delete "Dantagard" and insert -- Dantogard --, therefor.

Line 67, delete "kerotolytic" and insert -- keratolytic --, therefor.

Line 67, delete "(2,5-iioxo" and insert -- (2,5-dioxo --, therefor.

Column 12
Line 1, delete "know" and insert -- known --, therefor.

Column 17
Line 39, delete "Decription" and insert -- Description --, therefor.

Line 62, delete "Octyldimethlamine" and insert -- Octyldimethylamine --, therefor.

Column 18
Line 14, delete "Octyldimethlamine" and insert -- Octyldimethylamine --, therefor.

Signed and Sealed this
Second Day of June, 2015

Michelle K. Lee
*Director of the United States Patent and Trademark Office*